United States Patent [19]

Richardson et al.

[11] Patent Number: 5,221,606
[45] Date of Patent: Jun. 22, 1993

[54] REAGENT AND KIT FOR ENZYME ASSAY COMPRISING A SUBSTRATE CONSONANT WITH GIVEN ENZYME TO BE ASSAYED

[75] Inventors: Anthony C. Richardson, Henley-on-Thames; Brian V. Smith, Pinner; Robert G. Price, Northwood; Percy F. Praill, Brighton, all of United Kingdom

[73] Assignee: King's College London, London, England

[21] Appl. No.: 466,425

[22] PCT Filed: Sep. 7, 1988

[86] PCT No.: PCT/GB88/00737
§ 371 Date: Mar. 8, 1990
§ 102(e) Date: Mar. 8, 1990

[87] PCT Pub. No.: WO89/02473
PCT Pub. Date: Mar. 23, 1989

[30] Foreign Application Priority Data

Sep. 10, 1987 [GB] United Kingdom ............... 8721302

[51] Int. Cl.$^5$ ................... C12Q 1/00; C12Q 1/68
[52] U.S. Cl. .......................... 435/4; 435/7.4; 435/975
[58] Field of Search ............... 435/4, 7.4, 975

[56] References Cited

U.S. PATENT DOCUMENTS

| | | | |
|---|---|---|---|
| 3,719,480 | 3/1973 | Brantly et al. | 430/77 |
| 4,241,157 | 12/1980 | Webster et al. | 430/41 |
| 4,318,986 | 3/1982 | Richardson et al. | 435/18 |
| 4,694,070 | 9/1987 | Mitchell et al. | 530/329 |

FOREIGN PATENT DOCUMENTS

| | | |
|---|---|---|
| 0048834 | 4/1982 | European Pat. Off. |
| 0194472 | 9/1986 | European Pat. Off. |
| 79/00255 | 5/1979 | PCT Int'l Appl. |
| WO86/07061 | 12/1986 | PCT Int'l Appl. |
| 2008103B | 8/1982 | United Kingdom |
| 20794503 | 9/1982 | United Kingdom |

OTHER PUBLICATIONS

Pooler et al., Photochem. & Photobiol., vol. 30, pp. 581–584, 1979.
Piechoski et al., J. Phys. Chem., vol. 88, pp. 934–950, 1984.
Nakashima et al., Chem. Pharm. Bull, vol. 29, No. 6, pp. 1755–1758, 1981.
Gasha et al., vol. 92, No. 4, pp. 490–497, Yakugaku Zasshi, 1972.
Jesthi et al., J. Inst. Chemists (India), vol. 50, Nov. 78.
Andreasch, Monatscheft fur Chemie, 1908, 29, 399.
Ganitkevich and Turkewitsch, J. Gen. Chem. U.S.S.R. 1959, 29, 2061.
Tambor, Ber, 1900, 33, 864.
Weinschenk, Ber., 1901, 34, 1685.
Dox and Plaisance, J. Amer. Chem. Soc. 1916, 38, 2165.
Werner, J. Am. Chem. Soc., 1920, 42, 2309.
Phillips, J. Org. Chem, 1947, 12, 333.
Brooker, Keyes and Heseltine, J. Amer. Chem. Soc. 1951, 73, 5350.
Schneider and Pothman, 1941, 74B, 4761.
Wizinger and Wenning, Helv. Chem. Acta 1940, 23, 274.
Blazsek-Bodo, Vernes and Szurkos, Pharmacia (Bucharest), 1974, 22, 345.

*Primary Examiner*—Douglas W. Robinson
*Assistant Examiner*—Mike Meller
*Attorney, Agent, or Firm*—Larson and Taylor

[57] ABSTRACT

This invention relates to enzyme assays and substrates for use in such assays. The presence or absence of certain enzymes in vivo is a useful indicator of illness or deficiency in the organisms concerned. Enzymes are also useful in monitoring microbial growth in fermentors and in the food industry and are important in enzyme-linked immunosorbent assays (ELISA), and in the characterization of bacterial species in culture. Disclosed is a reagent for enzyme assay comprising a substrate consonant with a given enzyme to be assayed, labelled with a chromogenic group which, on action of the given enzyme, is liberated to give a colored product. Also disclosed is a kit for the assay of an enzyme comprising the reagent of the disclosed invention.

19 Claims, 1 Drawing Sheet

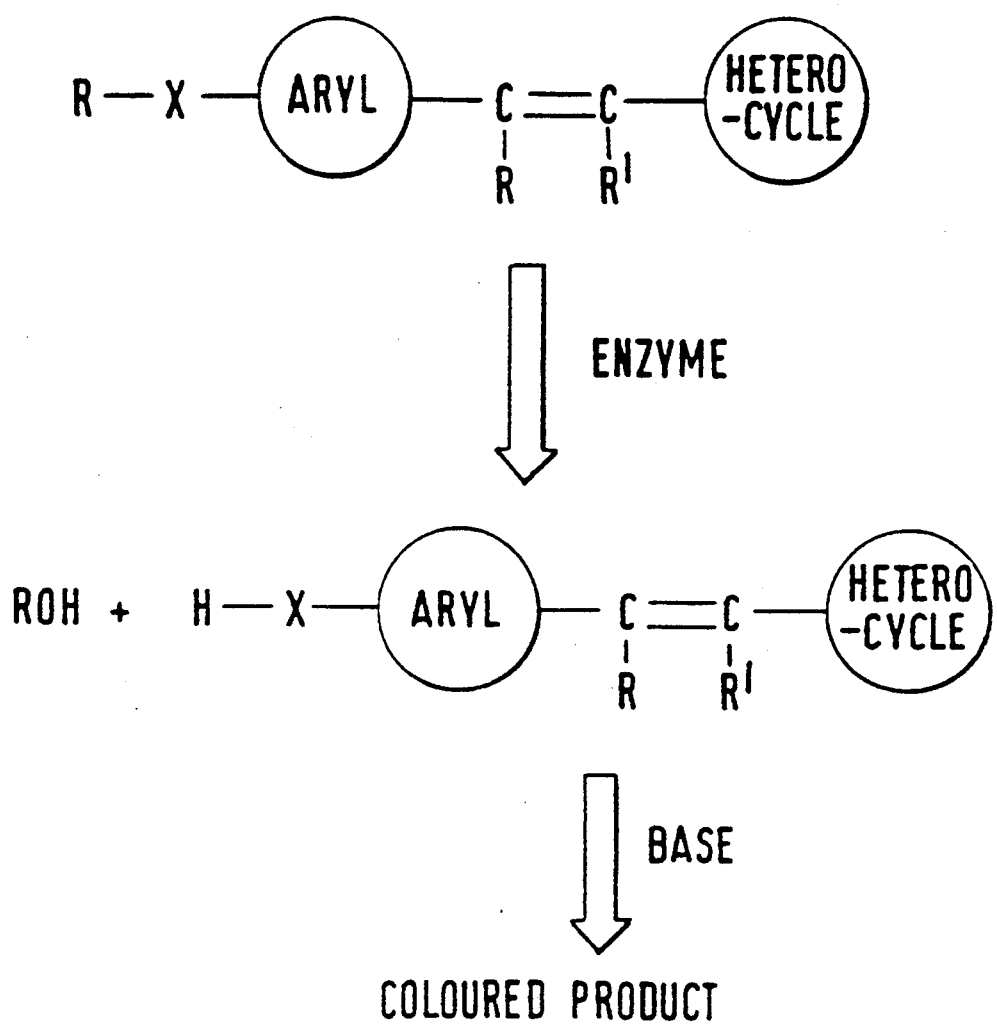

REAGENT AND KIT FOR ENZYME ASSAY COMPRISING A SUBSTRATE CONSONANT WITH GIVEN ENZYME TO BE ASSAYED

This invention relates to enzyme assays and substrates for use in such assays.

The presence or absence of certain enzymes in vivo is a useful indicator of illness or deficiency in the organism concerned. Enzymes are also useful in monitoring microbial growth in fermenters and in the food industry and are important in enzyme-linked immunosorbent assays (ELISA), and in the characterisation of bacterial species in culture.

A method of assaying enzymes is to prepare a substrate for each enzyme labelled with a releasable chromogenic group which is colourless or of pale colour when attached to the substrate, but which is strongly coloured when released by enzyme attack on the substrate (i.e. the reagent is of the form S—Z where S is the structural element recognised by the enzyme and Z is the chromogenic group released by enzymic cleavage of the S—Z bond).

U.K. Patent 2008103 described the use of certain nitrovinylphenyl derivatives for this purpose. However such nitrovinylphenyl derivatives suffer a number of disadvantages:

(i) Lack of sufficient water solubility. Usually with some of these nitrovinylphenyl substrates one cannot exceed 2 millimolar solution, and in the case of carboxylic acid esters of nitrovinylphenols, the solubility is very much less. Consequently, it is rarely possible to achieve sufficient solubility of the substrate to saturate the enzymes to be detected. Higher solubilities can be achieved in solvents such as methanol and dimethylsulphoxide, but enzymes are generally adversely affected by such solvents.

(ii) When the nitrovinylphenyl substrates need to be incorporated into kit form for easy and convenient use, they must be supplied as ready-made solutions, because of the difficulties associated with solubilising these substrates. This gives rise to problems of stability and a preferred method of presentation would be as a readily water-soluble solid, preferably in admixture with buffer salts, from which the user could conveniently make up the required substrate solution.

(iii) To develop fully the colour of the chromogenic nitrovinylphenol group, basic conditions are required, preferably pH 9.5. At such pH's, some chemical breakdown of the substrate is possible leading to the release of the chromogenic group, producing an undesirably high blank value to be offset.

(iv) At such high values of pH, nitrovinylphenols can undergo a Michael reaction or a reverse Nef reaction, leading to rapid fading of the generated colour and, at pH 9.5, experience has shown that the final readings have to be taken preferably within 5 minutes.

The applicants have aimed to overcome these disadvantages by providing enzyme substrates which are more water soluble than the nitrovinylphenol substrates, capable of releasing highly coloured chromogenic groups, the full colour of which is generated as close to neutral pH as possible, and is not susceptible to chemical breakdown in ordinary usage. In addition, substrates which afford insoluble chromogens are useful in some circumstances where the released chromogen is collected on a filter paper or membrane, or is strongly absorbed in such a way as to be water-fast. The colour of filter paper or membrane is then an indicator of the presence or absence of the particular enzyme (e.g. ELISA assays). This particular property is valuable in "dipstick" devices in which immobilisation of the chromogenic phenol is important in order to achieve an even colour.

According to this invention a reagent for enzyme assay comprises a substrate consonant with a given enzyme to be assayed, labelled with a chromogenic group which, on action of the given enzyme, is liberated to give a coloured product, characterised in that the chromogenic group has the general formula:

where Aryl is any aryl group, n is 0–3, R and R' are any compatible groups, Het is any heterocyclic group capable of extending the delocalisation of the electrons from the aryl group. X is NR or O, where R is H, alkyl or any suitable group that will not hinder the enzyme. Enzymes which may be assayed by the use of the appropriate substrates, include aryl esterases, carboxyesterases, lipases, acid and alkaline phosphatases, phosphodiesterases, sulphatases and glycosidases of many kinds, where the released groups would be of the form —O—Aryl—(CR=CR')$_n$—Het. This invention is not, however, limited to such enzymes and by choice of suitable substrate many other enzymes can in principle be determined. For example, substrates for peptidases and amino acid transferases of the form:

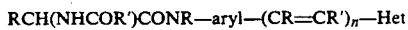

are envisaged, where the R and R' substituents are various compatible groups, and the released chromogen would be the aminoaryl derivatives HRN—Aryl—CR=CR'—Het.

The chromogenic product produced by enzyme action should preferably be of substantially different colour from the background colour associated with either unreacted substrate or the biological fluid being examined.

The phenols for use in the manufacture of substrates, or the substrates themselves may be prepared by condensation of a formylphenol or its O-substituted derivatives with activated heterocyclic ring methylene or methyl group of a suitable heterocyclic partner.

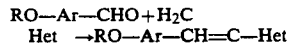

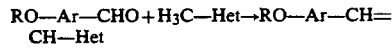

where Het=heterocycle, and Ar=aryl ring

Particularly preferred reagents are formed from O-acyl- and O-glycosyl derivatives of vanillin and syringaldehyde (or similar starting materials such as 4-hydroxybenzaldehyde or salicylaldehyde) by coupling with appropriate heterocycles such as rhodanine-3-acetic acid, 1,2-dimethylpyridinium iodide, 1,4-dimethylpyridinium iodide, 1,2-dimethylquinolinium iodide, 1,4-dimethylquinolinium iodide, 2-thiobarbituric acid, and 2,3-dimethylbenzothiazolium tosylate. This list is merely representative and not exclusive.

Such condensations have generally been effected under mild conditions using base catalysis (piperidine-ethanol, ammonium acetate-ethanol, potassium acetate-acetic acid-ethanol, except in the case of barbituric acid derivatives, where the reaction was catalysed by acid. It is believed that many similar reagents may be prepared by using these methods. In the examples described in this patent, the given formula describes only one of the two possible geometrical isomers about the double bond. In no case has the configuration been established unambiguously and both isomers are claimed.

The reagents of the invention release chromogenic products of distinctive colours, oranges, reds and blues, typically possessing $\lambda_{max}$ 450-700 nm and with a molar extinction coefficient $\epsilon$ greater than 20,000. If the assay is carried out using a spectrophotometer, then a high value for $\epsilon$ is desirable, but for visual estimation, such as in some ELISA based diagnostics (e.g. pregnancy tests) and in "dipsticks", the breadth of the envelope of absorption in the visible part of the spectrum is as important as $\epsilon_{max}$ and $\epsilon_{max}$ of less than 20,000 can be tolerated. Some enzymatically released chromogenic compounds in the present invention have wide envelopes of absorption and are therefore highly suitable for visual estimation.

The reagents of the invention include a wide range of compounds and include derivatives of chromogenic compounds well known to those engaged in the art of colour chemistry. Preferably these reagents are chosen in order to optimise solubility, facilitate enzyme-substrate interaction and to optimise the intensity of the released chromogenic molecules already referred to.

Preferred reagents according to the invention rely upon the presence of unsaturation based upon the aryl ring and conjugated to a heterocyclic system. The reagents preferably rely upon the presence of auxochromic groups in the aryl nucleus such as hydroxy or alkyloxy, the hydroxy function providing the link between the chromophore and the substrate portion of the molecule. The heterocyclic systems enhance the colour of the chromophore by a process of electron delocalisation.

BRIEF DESCRIPTION OF THE DRAWING

The drawing illustrates the general reaction scheme of the method of enzyme assay according to the invention.

DETAILED DESCRIPTION OF THE INVENTION

Preferred chromogenic groups which may be used in exercising the present invention include the following:

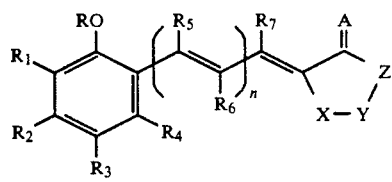
(Ia)

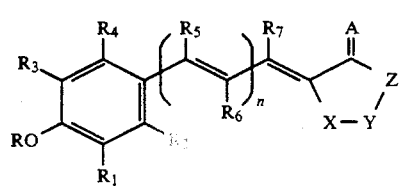
(Ib)

Where
n = 0 to 3;

R = acyl(R'CO—), (HO)$_2$OP—(or salt), HOSO$_2$—(or salt), glycosyl, or any other group capable of releasing the chromophore on enzyme action;

R$_1$-R$_7$ = any alkyl, alkoxy or other compatible group;
A = O, S or NH;
X = O, S or NH;
Y = C=S, C=O or C=NH;
Z = NH, N-alkyl, N-aryl, N—(CH$_2$)$_x$CO$_2$H and salts and esters thereof, N—(CH$_2$)$_x$NR'$_2$ and salts thereof, N—(CH$_2$)$_x$SO$_3$H and salts thereof, and N—(CH$_2$)$_x$NR'$_3$X (R'=alkyl);
x = 1 to 6.

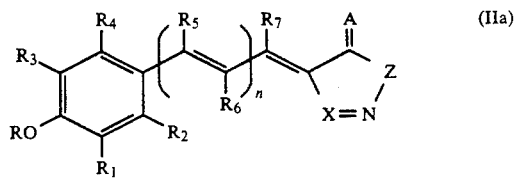
(IIa)

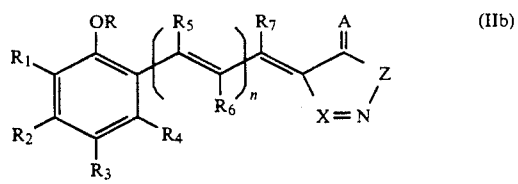
(IIb)

Where
n = 0 to 3;
R = acyl(R'CO—), (HO)$_2$OP—(or salt, HOSO$_2$—(or salt), glycosyl, or any other group capable of releasing the chromophore on enzyme action;
R$_1$-R$_4$ = H, alkyl or alkoxy
R$_5$-R$_7$ = H, alkyl or aryl
A = O, S or NH;
X = C-alkyl, C-aryl;
Z = NH, N-alkyl, N-aryl, N—C$_6$H$_4$SO$_3$H and salts thereof, N—(CH$_2$)$_x$CO$_2$H and salts, esters and amides thereof, N—(CH$_2$)$_x$SO$_3$H and salts thereof;
x = 1 to 10.

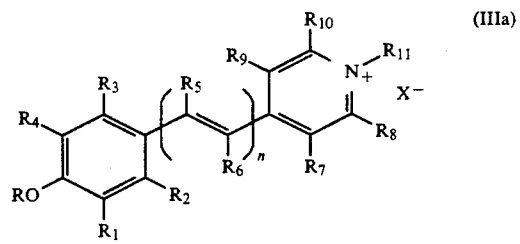
(IIIa)

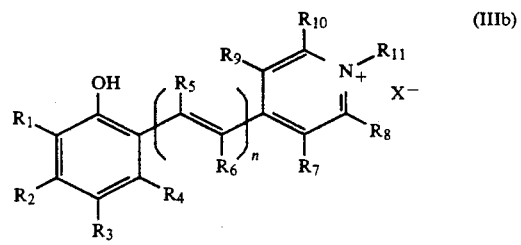
(IIIb)

-continued

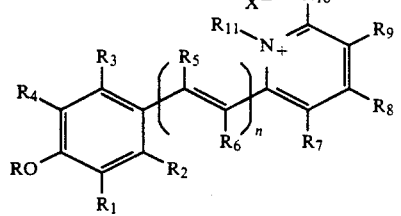
(IIIc)

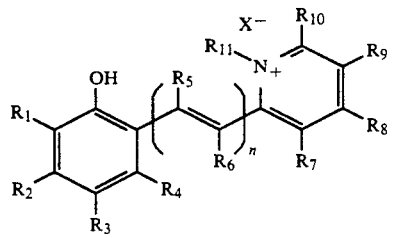
(IIId)

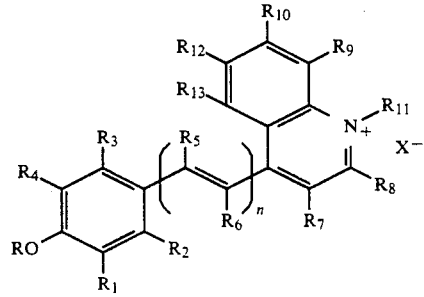
(IIIe)

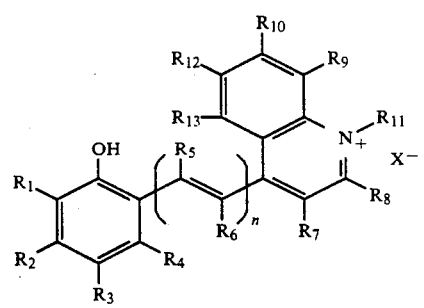
(IIIf)

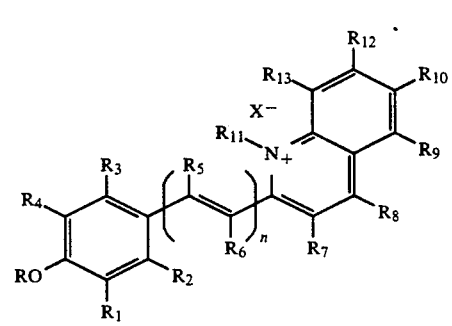
(IIIg)

-continued

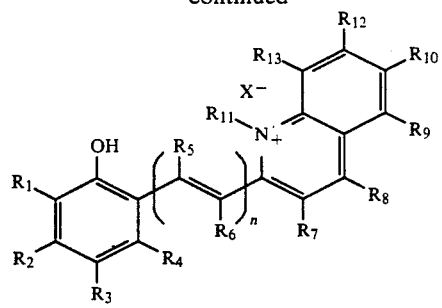
(IIIh)

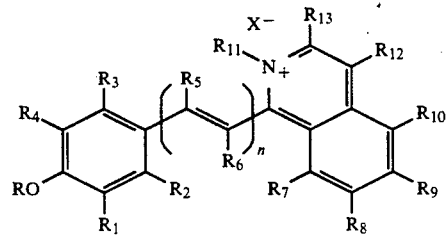
(IIIi)

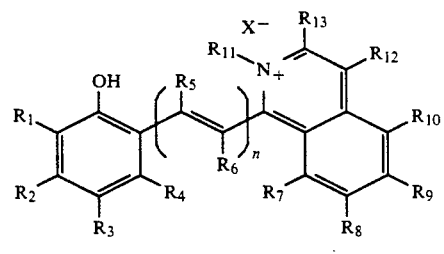
(IIIj)

where
n = 1 to 3;
R = acyl(R'CO—), (HO)$_2$OP—(or salt), HOSO$_2$—(or salt), glycosyl, or any other group capable of releasing the chromophore on enzyme action;
R$_1$–R$_4$ = H, alkyl or alkoxy;
R$_5$–R$_6$ = H, alkyl or aryl;
R$_7$–R$_{10}$ and R$_{12}$–R$_{13}$ = H, alkyl or aryl;
R$_{11}$ = alkyl; and
X = halide or other anion.

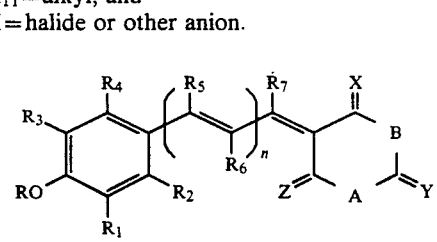
(IVa)

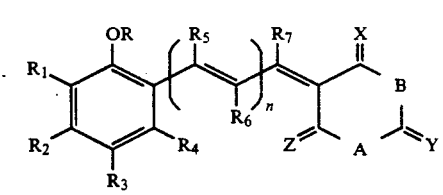
(IVb)

Where
n = 0 to 3;
R = acyl(R'CO—), (HO)$_2$OP—(or salt), HOSO$_2$—(or salt), glycosyl, or any other group capable of releasing the chromophore on enzyme action;
R$_1$–R$_4$ = H, alkyl or alkoxy;
R$_5$–R$_6$ = H, alkyl or aryl;
R$_7$ = H, alkyl, aryl or any compatible group;

A, B=NH, N-alkyl, N-aryl, N—C$_6$H$_4$SO$_3$H and salts thereof, N—(CH$_2$)$_x$CO$_2$H and salts, esters and amides thereof, N—(CH$_2$)$_x$SO$_3$H and salts thereof;

X, Y, Z=O, S, or NH;

x=1–10.

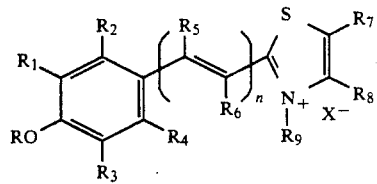
(Va)

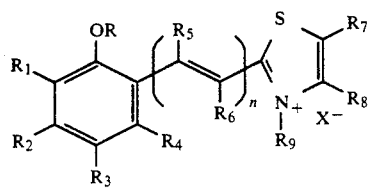
(Vb)

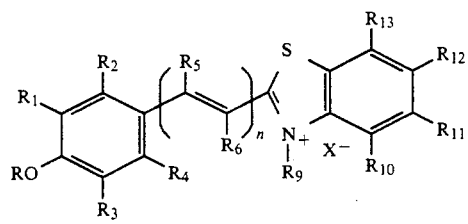
(Vc)

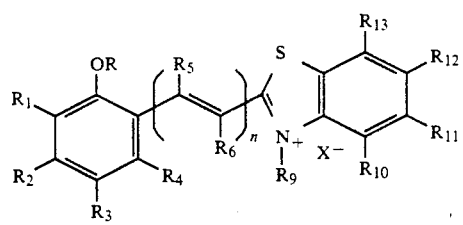
(Vd)

Where n=0 to 3;

R=acyl(R'CO—), (HO)$_2$OP—(or salt), HOSO$_2$—(or salt), glycosyl, or any other group capable of releasing the chromophore on enzyme action;

R$_1$-R$_4$=H, alkyl or alkoxy;

R$_5$-R$_6$=H, alkyl or aryl;

R$_7$-R$_8$=H, alkyl, aryl or any compatible group;

R$_9$=alkyl;

X=halide or other anion.

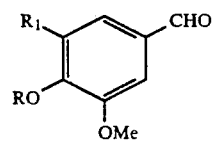
(VIa)

Where
(1) R$_1$=H;
(2) R$_1$=OMe

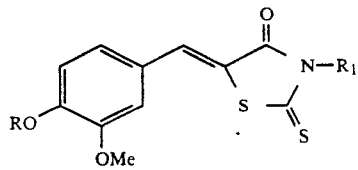
(VIb)

Where
(3) R$_1$=H
(4) R$_1$=Ch$_2$CO$_2$H
(5) R$_1$=C$_6$H$_4$—4—OH
(6) R$_1$=C$_6$H$_4$—4—CO$_2$H
(7) R$_1$=C$_6$H$_4$—4—SO$_3$H
(8) R$_1$=C$_6$H$_2$—3,4,5—OMe
(9) R$_1$=Me

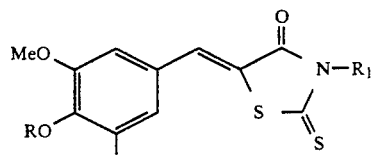
(VIc)

Where
(10) R$_1$=H
(11) R$_1$=CH$_2$CO$_2$H
(12) R$_1$=C$_6$H$_4$—4—OH
(13) R$_1$=C$_6$H$_4$—4—CO$_2$H
(14) R$_1$=C$_6$H$_4$—4—SO$_3$H
(15) R$_1$=C$_6$H$_2$—3,4,5—OMe
(16) R$_1$=Me

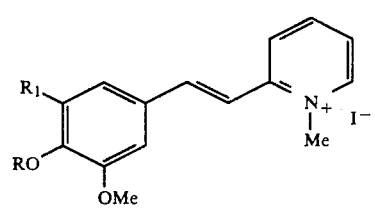
(VId)

Where
(17) R$_1$=H
(18) R$_1$=OMe

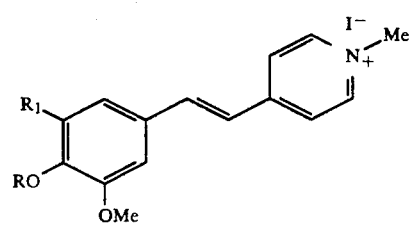
(VIe)

Where
(19) R$_1$=H
(20) R$_1$=OMe

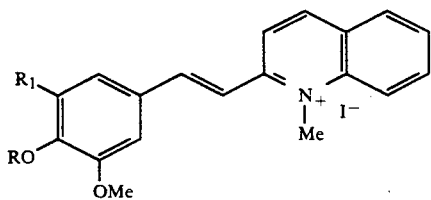

Where
(21) R₁=H
(22) R₁=OMe

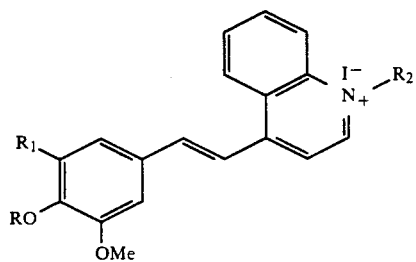

Where
(23) R₁=H, R₂=Me
(24) R₁=OMe, R₂=Me
(25) R₁=OMe, R₂=CH₃CH₂CH₂—

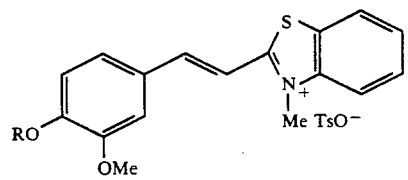

(26)

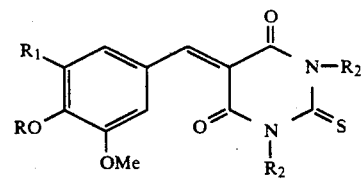

Where
(27) R₁=R₂=H
(28) R₁=OMe, R₂=CH₃CH₂

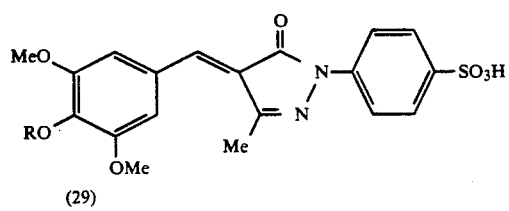

(29)

(VIf)

(VIg)

(VIh)

(VIi)

(VIj)

-continued

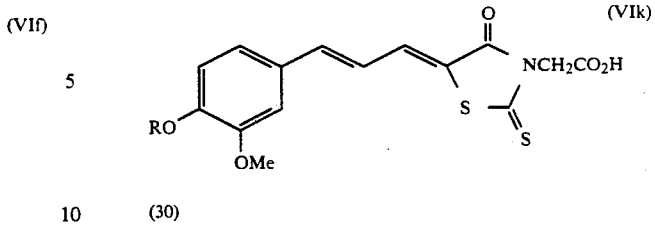

(30)

For compounds 1-30 in Figures via–vlk;
Series (a): R=H
Series (b): R=2-acetamido-2-deoxy-β-D-glucopyranosyl
Series (c): R=β-D-galactopyranosyl
Series (d): R=CH₃(CH₂)ₙCO—
Series (e): R=C₆H₅CO—
Series (f): R=(HO)₂PO—O—.

One particularly preferred class of reagents according to this invention include those based upon the 2-thioxothiazolidin-4-one (rhodanine) nucleus (Formula Ib), A=O, X=S, Y=C=S, Z=N(CH₂)ₓCO₂H or simlar compounds as a releasable substance. For example, the phenol (Formula Ib) R₁=OMe, R=R₂=R₃=R₄=R₇=H, n=0, A=O, X=S, Y=C=S, Z=NCH₂CO₂H has a conjugate base with λ$_{max}$ 490 nm, ε 32,600. By extension of the conjugation between the aryl and heterocyclic systems, the intensity of colour and λ$_{max}$ may be increased: thus the conjugate base of the phenol Formula Ib with R=R₂=R₃=R₄=R₅=R₆=R₇=H, R₁=OMe, N=1, A=C=O, X=S, Y=C=S, Z=CH₂CO₂H has λ$_{max}$ 524 (broad envelope 450-600 nm), molar extinction>40,000.

Amongst the reagents preferred for the release of a highly coloured substance, those shown in Formulas IIa-j and Va-d are valuable. Thus for Formula IIIA, with R, R₁-R₁₀=H. R₁₁= Me, n=1, X=I⁻ strong colour is associated with the formation of the conjugate base (λ$_{max}$ 444, ε 27,000) which shows strong solvatochromism. Thus, the conjugated base in organic solvents or in mixtures of water and organic solvents shows a well known marked bathochromic shift. In anhydrous pyridine λ$_{max}$ is 605 mm (ε 76,500).

Considerable enhancement of such colours is achieved with the incorporation of quinolinium nuclei or extension of conjugation as shown in Formulas IIIa-j. According to the invention, such colour and the enhancements referred to allow additional sensitivity in the assay of enzymes. In particular, compounds itemised in Formulas IIIa-j and Va-d, give extremely intense reds and blues and such colours may be intensified even further by the development of colour in the presence of organic solvents. Acetone is particularly good in this respect, and the presence of 20% v/v acetone in water produces a very marked bathochromic and hyperchromic shift. This effect is most marked in the case of compounds in Formulas IIa-j and Va-d, since complete delocalisation of the electrons of the phenoxide group can occur to give the merocyanine, formation of which is favoured by organic solvents:

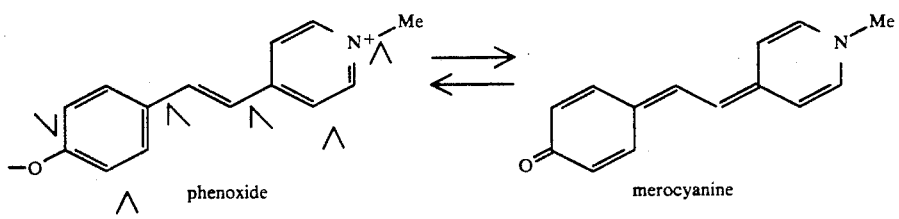

However, all of the other chromogenic phenols described show a small or moderate enhancement of colour intensity in the presence of acetone.

In current usage a stopping buffer of sodium carbonate and sodium hydrogen carbonate is used. However this has a major drawback in that it requires making up at the time of the assay. Long term storage of such an aqueous solution is not without drawbacks.

The properties of acetone have already been mentioned in regard to the marked bathochromic and hyperchromic shifts resulting from its use and accordingly the present invention provides a stopping buffer in the form of an acetone soluble base, in a mixture of acetone and water, for use as a stopping buffer. A preferred acetone soluble base is 1,4-diazabicyclo[2.2.2]octane (DABCO).

Other means of colour development of all the chromogenic phenols includes absorption on to a solid phase containing basic groups, e.g. diethylaminoethylcellulose (DEAE-cellulose).

The substrates, and more so the conjugate bases of most of the compounds described in Formulas IIIa-j and Va-d are selectively absorbed on to cellulose and related polymers under mildly basic conditions, giving intense colours which are not leached from the polymer by water. The colour formed on cellulose is quite different from that in solution and resembles the colour of the merocyanine. Such a property makes them valuable chromogens for use in "dipstick" devices and ELISA diagnostic kits.

Samples which may be conveniently assayed are those in fluid form, comprising biological fluids, e.g. serum, urine, samples derived from cell homogenates, micro-organisms, plant tissues, and enzyme conjugated antibodies and antigens.

The following illustrative examples show the preparation of substrate in accordance with the invention. There are also examples show analysis of esterase and N-acetyl-$\beta$-D-glucosaminidase (NAGase) respectively.

For the preparation of the glycosides, 4-formyl-2-methoxyphenyl 2-acetamido-2-deoxy-$\beta$-D-glucopyranoside and $\beta$-D-galactopyranoside, and related compounds (as described in U.K. Patent 2008103) were condensed with the appropriate heterocycle. The carboxylic ester substrates were prepared either by direct acylation of the chromogenic phenol, or by condensation of heterocycle with the appropriate ester of the hydroxybenzaldehyde derivative. The phosphates were mainly prepared by direct phosphorylation of the appropriate chromogenic phenol.

Ammonium 5-[4-(2-acetamido-2-deoxy-$\beta$-D-glucopyranosyloxy-3-methoxyphenylmethylene]2-thioxothiazolidin-4-one-3-ethanoate (4b).

A stirred suspension of 4-formyl-2-methoxyphenyl 2-acetamido-2-deoxy-$\beta$-D-glucopyranoside (1b) (5.00 g, 0.014 mol) and 2-thioxothiazolidin-4-one-3-ethanoic acid (2.69 g, 0.014 mol) in aqueous 96% ethanol (350 ml) containing ammonia (d 0.88, 2.7 ml) and ammonium chloride (2.63 g, 0.049 mol) was heated at about 60°. The mixture soon turned yellow, but remained heterogeneous. The reaction was continued for 4 h when t.l.c. (chloroform-methanol, 5:2) indicated that the starting aldehyde had been converted into a yellow slower-moving product. The solution was filtered and the yellow solid washed with boiling methanol to give (4b)[6.6 g, 86%, m.p. 165°-173° C. (decomp.), $[\alpha]_D + 18°$ (c 1, DMSO)], as a fine microcrystalline solid (Found: C, 44.65; H, 5.33; N, 7.28. $C_{21}H_{27}N_3O_{10}S_2.H_2O$ calc: C, 44.75; H, 5.19; N, 7.4%).

This compound was an excellent substrate for NA-Gase ($K_m$ 0.98 mM) and solutions of up to 10 mM in water could be achieved. The released phenol had $\lambda_{max}$ ($H_2O$, pH 10) 490 nm, $\epsilon$ 32600; $\lambda_{max}$ (0.2M DABCO in 4:1 water-acetone) 505 nm, $\epsilon$ 42,000, and the colour did not fade at pH 10 or below.

When the above condensation was repeated in methanol using potassium acetate as catalyst, the corresponding potassium salt was obtained in 25% yield as a yellow solid. When the condensation was repeated using acetic acid-potassium acetate as catalyst, followed by acidification with an excess of acetic acid, the free acid was obtained in good yield (m.p. 170°-172°).

4-Formyl-2,6-dimethoxyphenyl 2-acetamido-3,4,6-tri-O-acetyl-2-deoxy-$\beta$-D-glucopyranoside.

A solution of 2-acetamido-3,4,6-tri-O-acetyl-2-deoxy-$\alpha$-D-glucopyranosyl chloride (18.3 g, 50 mmol) in acetone (100 ml) was added to a solution of syringaldehyde (9.1 g, 50 mmol) in 1M potassium hydroxide solution (100 ml). The mixture was then stirred for 18 h and then diluted with water. The precipitated crystalline solid (10.8 g, 42%) was then filtered off, washed well with water and recrystallised from acetone-water water to give the title compound, m.p. 222°-225°, $[\alpha]_D + 3°$ (c 0.9, CHCl$_3$)

4-Formyl-2,6-dimethoxyphenyl 2-acetamido-2-deoxy-$\beta$-D-glucopyranoside (2b).

A stirred suspension of the above triacetate (7.6 g, 15 mmol) in methanol (500 ml) was treated with M-sodium methoxide (2 ml). The solid dissolved within 30 min to give a pale yellow solution from which the title compound started to separate out as a lumpy gelatinous solid. The supernatant was then decanted off and the addition of water (50–100 ml) caused the solid to become more granular and crystalline. The solid was then filtered off giving the title compound 2b, which was washed well with water, acetone and then finally with ether. It was then recrystallised from hot water, m.p. 186°-189° C., $[\alpha]_D + 13°$ (c 0.85, H$_2$O)

Ammonium 5-[4-(2-acetamido-2-deoxy-β-D-glucopyranosyloxy-3,5-dimethoxyphenylmethylene]-2-thioxothiazolidin-4-one-3-ethanoate (11b).

A suspension of 4-formyl-2,6-dimethoxyphenyl 2-acetamido-2-deoxy-β-D-glucopyranoside (2b)(0.50 g, 1.3 mmol) and 2-thoxothiazolidin-4-one-3-ethanoic acid (0.25 g, 1.3 mmol) in 96% aqueous ethanol (90 ml) containing ammonia (d 0.88, 0.25 ml, 4.5 mmol) and ammonium chloride (0.25 g, 4.7 mmol) was stirred at room temperature for 4.5 d when t.l.c (chloroform-methanol, 5:2) indicated that the starting aldehyde had been converted into a yellow slower-moving product. The solution was filtered and the collected solid washed with ethanol to give 11b (0.7 g, 87%) m.p. 150°–155° C. (decomp.), $[\alpha]_D = 38°$ (c 0.8, DMSO) as a fine crystalline yellow solid.

The substrate was soluble in water and was a fair substrate for NAGase. The released phenol had $\lambda_{max}$ (H$_2$O, pH 10) 515 nm, ε 44,000, $\lambda_{max}$ (0.2M DABCO in 4:1 water-acetone) 529 mm, ε 47,500 and the colour did not fade at pH 10 or below.

Ammonium 5-[4-(β-D-galactopyranosyloxy)-3-methoxyphenylmethylene]-2-thioxothiazolidin-4-one-3-ethanoate (4c).

A stirred suspension of 4-formyl-2-methoxyphenyl α-D-galactopyranoside (1c)(0.65 g, 2.0 mmol) and 2-thioxothiazolidin-4-one-3-ethanoic acid (0.39 g, 2.0 mmol) in aqueous 96% ethanol (150 ml) containing ammonia (d 0.88, 0.4 ml) and ammonium chloride (0.4 g, 7 mmol) was heated under reflux for 3 h when t.l.c. (chloroform-methanol 5:2) indicated that the starting material had been completely converted into a yellow slower-moving product. The solution was filtered and the collected solid washed with ethanol to give 4c as a fine yellow solid {0.95 g, 97%, m.p. 176°–180° C., $[\alpha]_D -35°$ (c 1, DMSO)} (Found: C, 45.26; H, 4.78; N, 5.32. $C_{19}H_{24}N_2O_{10}S_2$ calc: C, 45.23; H, 4.79; N, 5.55%).

The compound was easily soluble in water and was a very good substrate for *E. Coli* β-galactosidase.

Ammonium 5-[4-(β-D-galactopyranosyloxy)-3,5-dimethoxyphenylmethylene]-2-thioxothiazolidin-4-one-3-ethanoate (11c).

To a suspension of 4-formyl-2,6-dimethoxyphenyl β-D-galactopyranoside (2c) [0.17 g, 0.5 mmol, prepared similarly to (1c)] in methanol (10 ml) containing ammonium acetate (0.09 g, 1 mmol) was added 2-thioxothiazolidin-4-one-3-ethanoic acid (0.1 g, 0.5 mmol) and the mixture heated under gentle reflux. After 30 min. The solution become homogenous and after 4 h a product began to separate. After a further 1 h the mixture was cooled and the product filtered off and washed well with methanol to give 11c (0.16 g, 58%), m.p. 173°–174° C., $[\alpha]_D + 2.2°$ (c. 0.8, DMSO).

Ammonium 5-[4-(2-acetamido-2-deoxy-β-D-glucopyranosyloxy)-3-methoxyphenylmethylene]-2-thioxothiazolidin-4-one-3-benzene-4-carboxylate (6b)

2-Thioxothiazolidin-4-one-3-(benzene-4-carboxylic acid) (0.27 g, 1.1 mmol) was added to a stirred suspension of 4-formyl-2-methoxyphenyl 2-acetamido-2-deoxy-β-D-glucopyranoside (1b)(0.38 g, 1.1 mmol) in methanol (25 ml) containing ammonia (d 0.88, 2 drops) and ammonium chloride (0.21 g, 4.0 mmol) to give a yellow heterogeneous mixture. The reaction mixture was boiled under gentle reflux for 8 h after which t.l.c. (chloroform:methanol, 5:2) showed all the starting material had been converted to a slower-moving yellow product. The mixture was allowed to cool and the product filtered off and washed well with methanol to afford a yellow powder (0.3 g). m.p. 209°–212° C. (decomp). $[\alpha]_D + 17°$ (c 0.48, DMOS).

5-[4-(2-acetamido-2-deoxy-β-D-glucopyranosyloxy)-3-methoxyphenylmethylene]-3-(4-hydroxyphenyl)-2-thioxothiazolidin-4-one (5b)

3-(4-Hydroxyphenyl)-2-thioxothiazolidin-4-one (0.23 g, 1.0 mmol) was added to a stirred suspension of 4-formyl-2-methoxyphenyl 2-acetamido-2-deoxy-β-D-glucopyranoside (1b)(0.32 g, 0.9 mmol) in absolute ethanol (10 ml) containing ammonium acetate (0.08 g, 1.0 mmol) and the pale yellow heterogeneous reaction mixture boiled gently. After 5 h the mixture was cooled in ice and the yellow product was filtered off and washed well with methanol and acetone to give 5b (0.42 g, 74%), m.p. 234°–236° C., $[\alpha]_D + 2.5°$ (c 0.81, DMOS) Found: C, 53.62; H, 4.65; N, 4.73, $C_{25}H_{26}N_2O_9S_2$ calc: C, 53.38; H, 4.63; N, 4.98).

5-(4-propanoyloxy-3-methoxyphenylmethylene)-2-thioxothiazolidin-4-one (3d, n=1)

(a). To a solution of vanillyl propionate (1d, n=1)(2g, 10.3 mmol) and 2-thioxothiazolidin-4-one (rhodanine)(1.39 g, 1.03 mmol) in ethanol (20 ml) was added piperidine (5 drops). The mixture was heated under reflux for 2 h. during which time separation of the product occurred. The reaction mixture was cooled and the light yellow needles of (3d, n=1) were filtered off (m.p. 209°–210° C., 65% yield)

The product was slightly soluble in water, and at pH 8 it was cleaved by carboxyesterase to give the phenol (3a)($\lambda_{max}$ 488, ε 32,000).

(b). The propionate could also be made by the direct acylation of the phenol (3a) with either propionic anhydride or propanoyl chloride in pyridine. This procedure was generally preferred since it affoded a product with none of the chromogenic phenol as contaminant.

5-(Butanoyloxy-3,5-dimethoxyphenylmethylene)-2-thioxothiazolidin -4-one-3-ethanoic acid (11d, n=2)

To a solution of syringaldehyde butyrate (2, n=2)(1.5 g, 6 mmol) in absolute ethanol (50 ml) was added 2-thioxothiazolidin-4-one-3-acetic acid (rhodanin-N-acetic acid)(1.1 g, 5.75 mmol) and anhydrous potassium acetate (0.9 g, 9.2 mmol). The mixture was heated under gentle reflux for 1.5 h, and on cooling the potassium salt of the product separated out. The entire mixture was then diluted with water (25 ml) and concentrated hydrochloric acid (25 ml) to give the free acid (11d, n=2)(m.p. 193°–194° C., 60%). The ester could also be prepared by direct acylation of (11a) with butanoyl chloride in pyridine.

The ester readily dissolved in alkaline buffers (pH 8 etc.) to give a yellow solution which was readily cleaved by carboxyesterase to give the chromophoric phenol 11a.

The compound could be isolated as the potassium salt, but this was less stable than the free acid and slowly decomposed on standing; solutions in excess of 2 mM could be obtained from the potassium salt Several related esters were made in a related manner using the appropriate ester of syringaldehyde.

The decanoyl ester (11d, n=8) was prepared as the free acid in 78% yield, m.p. 118°–119° C. and was a good substrate for various lipases The benzoate ester (11e) was prepared in 80% yield as the potassium salt m.p. >230° C. and was an excellent substrate for carboxyesterase ($K_m$ 0.33)

Piperidinium 5-[3-(4'-ethanoyloxy-3'-methoxyphenyl)-prop-2-enylidene]-2-thioxothiazolidin-4-one-3-ethanoate (30)

4-Ethanoyloxy-3-methoxycinnamaldehyde (30 mg, 0.14 mmol) and rhodanine-N-acetic acid (30 mg, 0.16 mmol) were warmed together in ethanol (1 ml) containing a small drop of piperidine. After 30 min a yellow sticky solid separated from the reaction mixture which was then cooled in ice; the solid become more granular and was filtered off, washed with a little water and dried to give the ester as the piperidinium salt in 20% yield, m.p. 225°–226° C. The ester was hydrolysed on incubation with carboxyesterase to give the appropriate phenol, $\lambda_{max}$ 524 nm ($\epsilon$ 41,000)

3-(4-carboxyphenyl)-5-(3,5-dimethoxy-4-propanoyloxyphenylmethylene)-2-thioxothiazolidin-4-one (13d, n=1)

To a stirred solution of syringaldehyde propionate (0.238 g, 1 mmol) in methanol (15 ml) containing a small drop of piperidine was added 3-(4-carboxyphenyl)-2-thioxothiazolidin-4-one ((0.25 g, 1 mmol). The yellow heterogeneous mixture was then heated under gentle reflux for 6 h. Although t.l.c. ($CHCl_3$:MeOH, 5:1) indicated that some starting materials were still present, the insoluble product was filtered off to give the required adduct (13d, n=1)(0.2 g, 43%), m.p. 290°–293° C. (Found: C, 55.87; H, 4.01; N, 3.09. $C_{22}H_{19}NO_7S_2$ requires C, 55.87; H, 4.01, N, 2.95%)

The ester reacted with carboxyesterase to give the appropriate phenol, $\lambda_{max}$ 535 nm ($\epsilon$ 20,000).

The following esters were prepared using the appropriate ester of syringaldehyde:

Butanoate. m.p. 287°–289° C. (Found: C, 58.81; H, 4.34; N, 3.03. $C_{23}H_{22}O_7NS_2$ calc: C, 56.67; H, 4.31; N, 2.87%)

Acetate. m.p. >230 (Found: C, 53.83; H, 3.81; N, 3.10. $C_{21}H_{17}O_7NS_2$ Calc: C, 54.90; H, 3.73; N, 3.05%).

Nonanoate. m.p. 176°–180° C. (Found: C, 61.01; H, 5.58; N, 2.50. $C_{28}H_{31}O_7NS_2$ Calc: C, 60.43; H, 5.40; N, 2.51.).

Benzoate. m.p.>250° C. (Found: C, 60.01; H, 3.77; N, 2.70. $C_{26}H_{19}NO_7S_2$ Calc: C, 59.88; H, 3.64; N, 2.68%).

This class of esterase substrates exhibited high enzymatic activity with various esterases but had only moderate solubility in aqueous media. The nonanoate also exhibited enzymatic activity with lipase.

3-(4-Carboxyphenyl)-5-(4-β-D-galactopyranosyloxy-3-methoxyphenylmethylene)-2-thioxothiazolidin-4-one (6c)

To a stirred suspension of 4-formyl-2-methoxyphenyl β-D-galactopyranoside (1c)(0.47 g, 1.5 mmol) in absolute ethanol (25 ml) containing piperidine (1 drop), was added the potassium salt of 3-(4-carboxyphenyl)-2-thioxothiazolidin-4-one (0.44 g, 1.5 mmol) and the suspension was heated under gentle reflux for 2 h. A yellow solid separated which was filtered hot and washed with small portions of boiling methanol and ethyl acetate followed by ether to give the product (0.2 g, 22%) as the potassium salt, m.p. decomp.>230° C.

Potassium 5-(4-benzoyloxy-3,5-dimethoxyphenylmethylene)-2-thioxothiazolidin-4-one-3-(phenyl-4-sulphonate)(14e)

Syringaldehyde benzoate (2e)(0.286 g, 1 mmol) was dissolved in methanol (20 ml) containing a small drop of piperidine. Potassium 2-thioxothiazolidin-4-one-3-(4-phenylsulphonate) monohydrate (0.33 g, 1.01 mmol) was added and the solution heated under gentle reflux for 4 h. The mixture was then cooled, filtered and the product washed successively with methanol and ethyl acetate to give 14e in 53% yield. m.p.>300° C. (Found: c, 48.61; H, 3.35; N, 2.42. $C_{25}H_{18}NO_8S_3K.H_2O$ calc.: C, 48.92; H, 3.28; N, 2.28%).

The ester was hydrolysed by carboxyesterase to give the appropriate phenol $\lambda_{max}$ 545 nm ($\epsilon$ 21,000).

2-Thioxo-3-(3,4,5-trimethoxyphenyl)-5-(3,5-dimethoxy-4-phosphoroyloxyphenylmethylene)-thiazolidin-4-one (15f).

To an ice cold suspension of 5-(4-hydroxy-3,5-dimethoxyphenylmethylene)-2-thioxo-3-(3,4,5-trimethoxyphenyl)thiazolidine-4-one [15a, 0.23 g, 0.5 mmol, prepared in the conventional manner by condensation of syringaldehyde and N-(3,4,5-trimethoxyphenyl)-rhodanine] in anhydrous pyridine (2 ml) was added phosphorus oxychloride (0.07 ml, 0.8 mmol). The mixture was stoppered and allowed to warm to room temperature.

After 3 h. the reaction mixture was decomposed by the addition of crushed ice, whereupon a thick yellow precipitate was formed. The mixture was stirred for a further 1 h and acetone (10 ml) was then added and the precipitate filtered off and washed well with methanol to give (15f) (0.35 g, 40%), m.p. 293°–297° C. (Found C, 45.51; H, 4.42; N, 3.61. $C_{21}H_{22}NO_{10}PS_2.H_2O$ calc.: C, 44.91; H, 4.27; N, 2.49%).

It was moderately soluble in alkaline buffers, and was hydrolysed by alkaline phosphatase at pH's around 9 to give an insoluble yellow precipitate of the phenol, which dissolved in DABCO buffer containing acetone to give an intense blue colour ($\lambda_{max}$ 600 nm, $\epsilon$ 22,100)

5-(4-Phosphoroyloxy-3-methoxyphenylmethylene)-2-thioxo-3-methylthiazolidine-4-one (9F), pyridinium salt.

To an stirred ice cooled suspension of 5-(4-hydroxy-3-methoxyphenylmethylene)-2-thioxo-3-methylthiazolidine-4-one (0.61 g, 1.4 mmol) in dry pyridine (10 ml) was carefully added phosphoroyloxy chloride (0.20 ml, 2.2 mmol) over a period of 2 min. The solution turned yellow. When the addition was complete the reaction mixture was allowed to reach room temperature. It was allowed to stand 6 h after which ice was added. The suspended solids immediately dissolved, but soon after a yellow precipitate formed. The solvents were removed on a rotary evaporator and propan-2-ol added in order to precipitate more of the product. The suspension was then warmed on a water bath, and the warm solution (40° C.) filtered and the solid was washed with acetone and ether to give 0.36 g of the phosphate ester as a yellow powder. A second crop (0.12 g) of the product was obtained from the filtrate.

The phosphate was very soluble in water and was hydrolysed readily by alkaline phosphatase to give an insoluble yellow precipitate, which dissolved up on the addition of stronger alkali to give a red solution ($\lambda_{max}$ 507, $\epsilon$ 38,600)

The corresponding derivative derived from syringaldehyde, namely, 5-(4-Phosphoroyloxy-3,5-dimethoxyphenylmethylene)-2-thioxo-3-methylthiazolidine-4-one (16f) was prepared in the same manner. The phosphate was shown by elemental analysis and 360 MHz $^1$H-n.m.r. spectroscopy to be a mixture of the monopyridinium salt and free acid with approximately two moles of water of crystallisation. The phenol liberated by the action of phosphatase ($K_m$ 0.33 mM), was similarly insoluble in aqueous media, but soluble in DABCO in acetone; ($\lambda_{max}$ 533 ($\epsilon$40,300).

5-(4-β-D-Galactopyranosyloxy-3-methoxyphenylmethylene)-3-(4-hydroxyphenyl)-2-thioxothiazolidin-4-one (5c)

3-(4-Hydroxyphenyl)-2-thioxothiazolidin-4-one (0.23 g, 1.0 mmol) was added to a suspension of 4-formyl-2-methoxyphenyl β-D-galactopyranoside (1c)(0.32 g, 1.0 mmol) in methanol (20 ml) containing a drop of piperidine. The mixture, which rapidly turned yellow, was gently heated under reflux and deposited a thick precipitate after 30 min. The mixture was then cooled and filtered to give the required product (5c){0.12 g, 23%, m.p. decomp.>230° C., $[\alpha]_D$−34.4° (c 0.6, DMOS)} (Found: C, 53.04; H, 4.55; N, 2.81. $C_{23}H_{23}NO_9S_2$ requires C, 52.96; H, 4.44; N, 2.68%).

The released phenol on incubation with β-D-galactosidase had $\lambda_{max}$ 535 nm ($\epsilon$ 44,000).

4-[2(4-Benzoyloxy-3,5-dimethoxyphenyl)-vinyl]-1-methylquinolinium iodide (24e)

A mixture of syringaldehyde benzoate (2e)(0.18 g, 0.63 mmol), 1,4-dimethylquinolinium iodide (0.18 g, 0.63 mmol) and ammonium acetate (0.15 g, 1.9 mmol) was dissolved in warm ethanol and heated under reflux. The solution rapidly turned yellow and within 15 min, yellow precipitate formed. The reaction was continued for a further 1 h and then filtered. The collected solid was washed with methanol to give (24e)(0.28 g, 81%) as a fine yellow powder, m.p. decomp.>250° C. (Found: C, 58.86; H, 4.25; N, 2.71. $C_{27}H_{24}NO_4I$ calc. C., 58.60; H, 4.37; N, 2.53%).

The ester was a substrate for esterases, but the solubility in water was low (<0.25 mM).

4-{2-[4-β-D-Galactopyranosyloxy)-3-methoxyphenyl]-vinyl}-1-methylpyridinium iodide (19c)

4-Formyl-2-methoxyphenyl β-D-galactopyranoside (1c)(0.48 g, 1.5 mmol), 1,4-dimethylpyridinium iodide (0.32 g, 1.5 mmol) and ammonium acetate (0.35 g, 4.5 mmol) were dissolved in methanol (10 ml) and heated at reflux temperature to give a solution which progressively turned yellow. After about 2 h, a yellow precipitate started to form. The reaction was continued for a further 2 h when t.l.c. (chloroform-methanol, 5:4) indicated that almost all of the aldehyde had been converted into an almost non-mobile product. The reaction mixture was cooled to room temperature, the precipitate filtered off and washed with a little methanol to give (19c) as a yellow solid (0.28 g, 34%) m.p. 237°-242° C., $[\alpha]_D$−16° (c 1, DMSO)(Found: C, 47.68; H, 4.99; N, 2.86. $C_{21}H_{26}INO_7$ calc. C, 47.47; H, 4.93; N, 2.64%).

The galactoside was a substrate for E. Coli β-galactosidase and had a fair solubility in water.

2-{2-[4-(2-Acetamido-2-deoxy-β-D-glucopyranosyloxy)-3-methoxyphenyl]-vinyl}-1-methylquinolinium iodide (21B)

To a stirred suspension of 4-formyl-2-methoxyphenyl 2-acetamido-2-deoxy-β-D-glucopyranoside (1b)(0.21 g, 0.59 mmol) in ethanol (10 ml) containing ammonium acetate (0.14 g, 1.8 mmol) and ammonia (d 0.88, 0.2 ml) was added 1,2-dimethylquinolinium iodide (0.16 g, 0.56 mmol). The mixture was heated at 60°-65° C. and a colour change to orange and then to brown was noted. After 4 h, the reaction mixture was cooled and the solid product filtered off and washed successively with ethanol, acetone and ether to give (21b) as an orange crystalline solid (0.23 g, 62%), m.p. 165° C. (decomp.), $[\alpha]_D$+19° (0.8, DMSO)(Found: C, 49.43; H, 5.45; N, 4.46. $C_{27}H_{31}N_2O_7.2H_2O$ calc.: C, 49.25; H, 5.36; N, 4.25%).

The compound was a substrate for NAGase and the released phenol had $\lambda_{max}$ ($H_2O$ pH 10) 515 nm ($\epsilon$ 42,500), (DABCO buffer) 535 nm ($\epsilon$ 46,500).

2-[2-(4-Benzoyloxy-3-methoxyphenyl)-vinyl-1-methylquinolinium iodide(21e)

A stirred solution of 1,2-dimethylquinolinium iodide (0.30 g, 1.1 mmol), syringaldehyde benzoate (2e)(0.31 g, 1.1 mmol) and ammonium acetate (0.10 g, 1.1 mmol) in methanol (15 ml) was heated under reflux to give a clear orange solution from which a yellow precipitate soon formed. After 1 h, the reaction mixture was cooled and the precipitate filtered off to give (21e)(0.45 g, 74%) as a yellow powder, m.p. 240°-245° C. (Found: C, 58.86; H, 4.25; N, 2.71. $C_{27}H_{24}INO_4$ calc. C, 58.60; H, 4.37; N, 2.53%)

The benzoate was moderately soluble in water (0.25 mM) and was readily cleaved by carboxyesterase at pH 8.

2-{2-[4-(β-D-Galactopyranosyloxy)-3-methoxyphenyl]-vinyl}-1-methylquinolinium iodide (21c)

A stirred suspension of 4-formyl-2-methoxyphenyl β-D-galactopyranoside (1c)(0.12 g, 0.37 mmol), 1,2-dimethylquinolinium iodide (0.10 g, 0.37 mmol) and ammonium acetate (0.06 g, 0.8 mmol) in ethanol (10 ml) was heated under reflux to give a heterogeneous mixture which soon turned orange. After 1 h, t.l.c. (chloroform-methanol 5:4) indicated that the aldehyde had been fully converted into an almost non-mobile orange product. The solution was cooled, filtered and the collected material was washed thoroughly with ethanol to give (21c)(0.16 g, 72%) as an orange crystalline solid, m.p. 225° C., $[\alpha]_D$−18° (c1, DMSO).

This compound had very good water solubility and was an excellent substrate for E. coli β-galactosidase ($K_m$ ca. 0.2) with 90% of $v_{max}$ achieved at a concentration of 0.5 mM. In buffer at pH 10 the released phenol had $\lambda_{max}$ 515 ($\epsilon$ 42,000) and in DABCO buffer it was 535 ($\epsilon$ 46,500)

4-{2-[4-(β-D-Galactopyranosyloxy)-3-methoxyphenyl]-vinyl}-1-methylquinolinium iodide (23c)

A suspension of 4-formyl-2-methoxyphenyl β-D-galactopyranoside (1c)(0.20 g, 0.63 mmol), 1,4-dimethylquinolinium iodide (0.18 g, 0.63 mmol) and ammonium acetate (0.15 g, 1.9 mmol) in ethanol (20 ml) was heated at 60°-70° C. with stirring for 1 h when t.l.c. (chloroform-methanol, 5:4) indicated that the aldehyde had been completely converted into the almost non-mobile yellow product. The reaction mixture was cooled, and filtered to give a yellow solid which was washed sequentially with ethanol, acetone and ether to give (23c) as mustard yellow solid (0.33 g, 90%), m.p. 216°-220° C. (decomp.), $[\alpha]_D$−17° (c 1, DMOS)-

(Found: C, 48.89; H, 5.28; N, 2.36. $C_{25}H_{28}INO_7.2H_2O$ calc.: C, 48.63; H, 5.22; N, 2.27%).

This compound had good water solubility, and was an excellent substrate for *E. Coli* β-galactosidase ($K_m$ 0.062), with 95% of $v_{max}$ being achieved at a concentration of 0.5 mM (at higher concentrations slight substrate inhibition was noted). In buffer at pH 10 the released phenol had $\lambda_{max}$ 525 (ε 35,000) and in DABCO buffer it was 560 (ε 37,000).

4-{2-[4-(2-acetamido-2-deoxy-β-D-glucopyranosyloxy)-3-methoxyphenyl]-vinyl}-1-methylquinolinium iodide (23b).

A stirred suspension of 4-formyl-2-methoxyphenyl 2-acetamido-2deoxy-β-D-glucopyranoside (1b)(0.25 g, 0.70 mmol), 1,4-dimethylquinolinium iodide (0.20 g, 0.70 mmol) in ethanol (20 ml) containing ammonium acetate (0.16 g, 2.1 mmol) and ammonia (conc.) (0.12 ml) was heated at 60°-70° C. The mixture soon turned orange and reaction was complete after 1.5 h as indicated by t.l.c. (chloroform-methanol, 5:4). The solid material was filtered off and washed sequentially with ethanol, acetone and ether to give (23b) as a fine yellow solid {0.34 g, 78%, m.p. 207°-212° C. (decomp.), $[\alpha]_D+28°$ (c 1, DMOS)}(Found: C, 52.12; H, 5.01; N, 4.78. $C_{27}H_{31}IN_2O_7$ calc. C, 52.10; H, 5.02; N, 4.50%).

The compound had good water solubility an was a fair substrate for NAGase

2-{2-[4-(β-D-Galactopyranosyloxy)-3-methoxyphenyl]vinyl}-1-methylpyridinium iodide (17c)

4-formyl-2-methoxyphenyl β-D-galactopyranoside (1c)(0.12 g, 0.38 mmol), 1,2-dimethylpyridinium iodide (0.12 g, 0.51 mmol) and methanolic sodium methoxide (1M, 0.38 ml, 0.38 mmol) in methanol (10 ml) was carefully heated until the reagents had completely dissolved, after which the reaction mixture was allowed to cool to room temperature. A yellow precipitate started to separate after about 2 h. The reaction mixture was left over-night (18 h), after which the precipitate was filtered off and washed well with methanol to give (17c)(0.11 g, 54%) as a fine yellow solid, m.p. 210°-230° C. (decomp.), $[\alpha]_D-14°$ (c 1, DMSO).

2-[2-(4-phosphoroyloxy-3-methoxyphenyl)-vinyl]-1-methylquinolinium iodide (21f)

To a stirred rusty-red solution of partly dissolved phenol, 2-[2-(4-hydroxy-3-methoxyphenyl)-vinyl]-1-methylquinolinium iodide (21a)(0.28 g, 0.67 mmol) in dry pyridine (5 ml) was carefully added phosphorus oxychloride (0.10 ml, 1.1 mmol). An exothermic reaction occurred, but the reaction mixture remained heterogeneous and did not markedly change colour. Small samples of the reaction mixture were regularly taken and basified to monitor the presence of unreacted phenol. After 3 h a considerable amount of phenol still appeared unreacted, so more phosphoroyloxy chloride (0.10 ml, 1.1 mmol) was added. The reaction was stirred for a further 30 min before being quenched by the addition of a little ice to hydrolyse the phosphorus oxychloride ester complex. The reaction mixture at first became homogeneous, but a small amount of an orange precipitate soon started to form. The pyridine-water solvent was evaporated on a rotary evaporator, and the residue shaken with ethanol from which a fine solid separated out. It was filtered off and washed with ethanol and acetone to give a yellow very hygroscopic product (0.14 g) which on exposure to moist air collapsed to a red syrup.

It was very soluble in water to give a pale yellow solution, which reacted rapidly with alkaline phosphatase to liberate the corresponding phenol. However, the extreme hygroscopic nature of this compound made rather unstable in storage.

2-[2-(4-phosphoroyloxy-3,5-dimethoxyphenyl)-vinyl]-1-methylquinolinium iodide (22f), pyridinium salt Phosphoroloxy chloride (0.10 ml, 1.0 mmol) was carefully added to an ice-cold stirred suspension of 2-[2-(4-hydroxy-3,5-dimethoxyphenyl)-vinyl]-1-methyquinolinium iodide (22a)(0.29 g, 0.65 mmol) in dry pyridine (5 ml). The ice cooling was removed after the addition was completed and the reaction was stirred for another 3 h. The mixture remained heterogeneous but during the reaction period, its colour changed from red to orange. The reaction mixture was then quenched with ice, whereupon the mixture became homogeneous but the product soon separated out as an orange solid. The mixture was evaporated to dryness and the resulting solid shaken with ethanol (50 ml), and then filtered off and washed successively with ethanol and acetone to give (22f)(0.25 g, ca. 66%) as an orange powder.

The product was very soluble in water and was good substrate for alkaline phosphatase ($K_m$ 0.68 mM), with 42% of $v_{max}$ being achieved at a concentration of 0.5 mM.

4-[2-(4-Phosphoroyloxy-3,5-dimethoxyphenyl)-vinyl]-1-propylquinolinium (25f).

To a stirred suspension of 4-[2-(4-hydroxy-3,5-dimethoxyphenyl-vinyl]-1-propylquinolinium iodide (25a)(0.59 g, 1.2 mmol) in ice-cold anhydrous pyridine (10 ml) was carefully added phosphoroyloxy chloride (0.12 ml, 1.2 mmol). As soon as the addition was complete, the mixture was allowed to warm to room temperature. The colour changed to red and the mixture become homogeneous. After 1½ h, it was decomposed with ice and stirred for 5 min before the pyridine and excess water was removed on a rotary evaporator. The resulting residual solid was finally extracted with ethanol to remove any residual pyridinium chloride, and filtered to give the phosphate as a zwitterion (0.40 g, 78%), m.p. 185°-195° C. (decomp.) as an orange powder, which turned dark red on storage (Found: C, 61.32; H, 5.69; N, 3.05. $C_{22}H_{23}NO_6P$ calc.: C, 61.68; H, 5.41; N, 3.27%).

The phosphate was water soluble and was an excellent substrate for alkaline phosphatase (Km 0.176) with 86% of $v_{max}$ being achieved at a concentration of 1 mM. The liberated phenol had $\lambda_{max}$ 555 nm ($H_2O$, pH 10) ε 33,800; $\lambda_{max}$ 605 nm (DABCO in 4:1 water-acetone) ε 38,100.

4-{2-[4-(β-D-Galactopyranosyloxy)-3,5-dimethoxyphenyl]-vinyl}-1-methylquinolinium iodide (24c)

A suspension of 4-formyl-2,6-dimethoxyphenyl β-D-galactopyranoside (2c)(0.20 g, 0.58 mmol), 1,4-dimethylquinolinium iodide (0.17 g, 0.58 mmol) in ethanol (20 ml) containing ammonium acetate (0.15 g 1.9 mmol) was stirred at about 60° C. for 5 h. The dark orange precipitate which formed during the reaction was then filtered off and washed with ethanol followed by acetone to give (24c)(0.25 g, 70%) an orange solid.

The product was easily soluble in water and was good a substrate for *E. Coli* β-galactosidase.

2-{2-[4-(β-D-Galactopyranosyloxy)-3,5-dimethoxyphenyl]-vinyl}-1-methylquinolinium iodide (22c)

A suspension of 4-formyl-2,6-dimethoxyphenyl β-D-galactopyranoside (0.19 g, 0.55 mmol), 1,2-dimethylquinolinium iodide (0.16 g, 0.55 mmol) in ethanol (20 ml) containing ammonium acetate (0.13 g, 1.7 mmol) was stirred at about 60° C. for 5 h. The dark orange precipitate which formed during the reaction was then filtered off and washed with ethanol followed by acetone to give (22c)(0.2 g, 86%) as an orange powder.

The product was easily soluble in water and was a good a substrate for E. Coli β-galactosidase.

4,6-dioxo-5-(4-propanoyloxy-3,5-dimethoxyphenylmethylene)-2-thioxo-1,3-diazacyclohexane (28d, n=1)

Syringaldehyde propionate (2d, n=1)(2.38 g) was dissolved in glacial acetic acid (20 ml) and a solution of 2-thiobarbituric acid (1.5 g) in hot acetic acid (10 ml) was added. The reaction mixture was heated under reflux for about 1 min, during which time it turned an orange-red colour and an orange solid separated out. The reaction mixture was allowed to stand at room temperature for 1 h, and the product then filtered off to give (28d, n=1)(2.8 g, m.p. 252°–254° C.).

The compound was a poor-to-moderate substrate for carboxyesterase, and its solubility in water was not particularly good.

Potassium 1-(benzene-4-sulfonate)-4-(4-Benzolyloxy-3,5-dimethoxyphenylmethylene)-3-methyl-5-pyrazalone (39e).

1-(Benzene-4-sulphonic acid)-3-Methyl-5-pyrazalone (0.16 g, 0.63 mmol) was dissolved in warm acetic acid (10 ml) containing potassium acetate (0.19 g, 1.9 mmol). The solution was cooled to room temperature and syringaldehyde benzoate (2e)(0.18 g, 0.63 mmol) was added. The solution rapidly turned orange, and an orange precipitate formed. After 3 h the precipitate was filtered off, and washed washed well with acetone to give (29e)(0.30 g, 90%) as an orange solid, m.p.>250° C. (Found: C, 51.17; H, 4.25; N, 4.62, $C_{26}H_{21}N_2O_8SK.3-H_2O$ calc. C, 50.81; H, 4.43; N, 4.56%).

The compound was a substrate for carboxyesterase.

1,3-Diethyl-4,6-dioxo-5-(4-phosphoroyloxy-3,5-dimethoxyphenylmethylene)-2-thioxo-1,3-diazacyclohexane (27F)

Disodium vanillyl phosphate (1f)(0.2 g, 0.725 mmol) [prepared according to Williams and Naylor, J. Chem. Soc. (Section B), 1971, 1973] was dissolved in water (4 ml) and conc. hydrochloric acid added (1drop) followed by 0.15 g (0.725 mmol) of 1,3-diethyl-2-thiobarbituric acid. The reaction mixture was kept at room temperature for 24 h. during which time a small amount of yellow solid had separated. This was ignored and the whole mixture was evaporated to dryness under reduced pressure to give a solid, which was recrystallised from water-acetone-ethyl acetate to give the phosphate (27f) in 54% yield, m.p.>250° C.

It had good solubility in water and TRIS buffer at pH 9 and was cleaved by alkaline phosphatase to give a bright red solution. The released phenol had $\lambda_{max}$ 514 nm ($\epsilon$ 31,000).

2-{2-[4-(β-D-Galactopyranosyloxy)-3-methoxyphenyl]-vinyl}-3-methylbenzothiazolium tosylate (26c).

4-Formyl-3-methoxyphenyl β-D-galactopyranoside (1c)(3.14 g, 0.01 mol) was dissolved in hot methanol (20 ml) and 2,3-dimethylbenzothiazolium tosylate (3.35 g, 0.01 mol) was added followed by a drop of piperidine. The mixture was heated under reflux for 2 h, during which time it become strongly coloured. The reaction mixture was then cooled and ether (200 ml) was added to precipitate the product as an orange solid, which was well washed with methanol to give (26c){4.8 g, 80%, m.p. 147°–149° C., $[\alpha]_D$ – 10.4'0 (c 1, DMSO)}. (Found: C, 55.66; H, 5.28; N, 2.11. $C_{30}H_{34}O_{11}NS_2$ Calc: C, 55.54; N, 5.28; N, 2.16.)

The galactoside was very soluble in water, and when a solution in buffer at pH 6.8 was treated with β-D-galactosidase from E. Coli it reacted to give an intense violet-red solution.

The pH optimum of the galactoside was pH 6.5, $K_m$ 0.23 mM, and 95% of $v_{max}$ was achieved at a concentration of 1 mM, but it started to show substrate inhibition above 0.7 mM. The released phenol had $\lambda_{max}$ 520 nm ($\epsilon$ 93,000) at pH 9.2. In DABCO buffer in the presence of 20% acetone it had $\lambda_{max}$ 540 nm ($\epsilon$ 100,000).

Formulation of a Kit for the Assay of N-Acetyl-β-D-Glucosaminidase in Biological Fluids (e.g. Urine)

The glucosaminide (4b) was finely powdered by grinding in a motar and pestle.

The mixture of buffer salts was prepared by grinding together citric acid monohydrate (74 g) and anhydrous dipotassium hydrogen phosphate (86 g) in either a macerater or coffee grinder. It is important that the two compounds be very intimately mixed, such that on dissolving 0.2 g in 10 ml water, a pH of 4.5±0.1 is obtained.

The above glucosaminide (4.1 g) was then mixed with with 100 g of the above buffer salt mixture, and the pale yellow solid mixed very thoroughly by shaking (MIXTURE A). When 0.2 g of this mixture was dissolved in 10 ml of water a 1.5 mM solution of the substrate in phosphate-citric acid buffer was obtained at pH 4.5±0.1.

The stopping buffer was made by dissolving 1,4-diazabicyclo[2.2.2]octane (DABCO)(112 g) in a mixture of acetone (800 ml) and water (200 ml).

The kit consists of two tightly stoppered bottles. The first bottle (12–20 ml capacity) contains 0.2 g of MIXTURE A and the second bottle contains 10 ml of the STOPPING BUFFER.

METHOD. The MIXTURE A is dissolved in 10 ml of distilled water to give SOLUTION A. The solution should be allowed to stand in a thermostatically controlled bath at 37° C., and then 0.75 ml of the solution is added to a series of suitable tubes of 2 ml capacity. To these tubes is added, with vigorous stirring, 0.50 ml aliquots of the urines under examination, and a blank is prepared by adding 0.05 ml of distilled water rather than urine to one of the tubes. The tubes are then incubate for a set length of time (preferably 30 min), after which 0.25 ml of the STOPPING BUFFER is added to each tube and the absorption (A) at 505 nm is determined for each sample, and adjusted for the value of the blank.

The enzyme activity of the enzyme in each sample is given by the expression using and $\epsilon_{max}=42,000$.

$$\text{Enzyme activity } (\mu M \cdot h^{-1} L^{-1}) = \frac{A \times 10^6 \times 1.05 \times 1 \times 1000}{\epsilon \times 1 \times 1000 \times t \times 0.05}$$
$$= (A/t) \times 1232$$

where t=time of incubation in hours

METHOD FOR THE ASSAY OF ARYLESTERASE IN SERUM

The propionate (11d, n=1)(22.4 mg) was dissolved in 100 ml of borate buffer at pH 8 [prepared by dissolving boric acid (3.09 g) and potassium chloride (3.73 g) in water (1000 ml) and adjusting the pH to 8 by the addition of 2M sodium hydroxide solution] to give a 0.5 mM solution of the substrate ($K_m$=0.025 mM)

The serum samples were diluted by a factor of 10 prior to the assay. The substrate solution and the diluted sera were then preincubated at 37° C. in a water bath. Aliquots (0.75 ml) of the substrate solution were then pipetted into small plastic tubes (2 ml capacity), and 0.05 ml samples of the sera were added to each of the substrate aliquots and shaken vigorously to ensure adequate mixing. A blank was run by substituting water (0.05 ml) for the serum. The reaction was stopped after 10 min by the addition of the stopping buffer (0.25 ml) [prepared by dissolving DABCO (22.4 g) in water (200 ml) and adjusting the pH to 10 by the addition of a little conc. hydrochloric acid. The resulting mixture was then made up to 1000 ml with acetone]. The absorption (A) was then measured at 529 nm and the enzyme activity calculated on the basis of an $\epsilon_{max}$=47,500.

$$\text{Enzyme activity } (\mu M \cdot h^{-1} L^{-1}) = \frac{A \times 10^6 \times 1.05 \times 1 \times 1000 \times 10}{\epsilon \times 1 \times 1000 \times t \times 0.05 \times 1}$$
$$= (A/t) \times 4421$$

where t=time of incubation in hours

ASSAY OF CARBOXYLIC ACID HYDROLASE E.C. 3.1.1.1

The benzoate ester (11e) was suitable for the assay of carboxyesterase, using a substrate concentration of 0.25 mM ($K_m$ 0.033 mM). Otherwise it was carried out in exactly the same ways as above $$\text{Enzyme activity } (\mu M \cdot h^{-1} L^{-1}) = \frac{A \times 10^6 \times 1.05 \times 1 \times 1000 \times 10}{\epsilon \times 1 \times 1000 \times t \times 0.05 \times 1}$$
$$= (A/t) \times 4421$$

We claim:

1. A reagent for assaying an enzyme comprising a substrate consonant with a given enzyme to be assayed, labelled with a chromogenic group which, on action of the given enzyme, is liberated to give a colored product, characterized in that the reagent is of the formula:

S—Z where S is a structural element substrate recognized by the enzyme, and Z is a chromogenic group released by enzymatic cleavage of the S—Z bond, and further characterized in that the released chromogenic group is of the formula:

—X—Aryl—(CR=CR')$_n$—Het where Aryl is any aryl group, n is 0-3, R and R' are any compatible group that does not hinder the enzyme, Het is any heterocylic group capable of extending the delocalization of electrons from the aryl group, and X is selected from the group —O— or —NR— where R is any compatible group that does not hinder the enzyme.

2. A reagent as claimed in claim 1, wherein said aryl group is a phenol group incorporating solubilizing (hydrophilic) groups.

3. A reagent as claimed in claim 1, wherein said heterocylic group (Het) is of the formula:

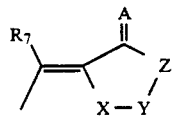

wherein
 A is selected from the group O, S, or NR where R is H, alkyl or any other compatible group that does not hinder the enzyme,
 X is selected from the group O, S, or NR where R is H, alkyl or any other compatible group that does not hinder the enzyme,
 Y is selected from the group C=O, C=S, or C=NR where R is H, alkyl or any other compatible group that does not hinder the enzyme,
 Z is any compatible nitrogen linked group that does not hinder the enzyme selected from the group consisting of NH; N-alkyl; N-aryl, N—(CH$_2$)$_x$-CO$_2$H, salts and esters; N—(CH$_2$)$_x$NR$_2$, and salts; N—(CH$_2$)$_x$SO$_3$H, and salts; and N—(CH$_2$)$_x$NR$_3$X, where R is alkyl, x is 1-6, and X is O, S, or NH and R$^7$ is H, alkyl, aryl or any compatible group that does not hinder the enzyme.

4. A reagent as claimed in claim 1, wherein said heterocyclic group (Het) is of the formula:

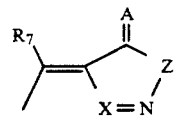

wherein
 A is selected from the group O, S, or NR where R is H, alkyl or any other compatible group that does not hinder the enzyme,
 X is selected from the group C-alkyl, C-aryl or any other compatible carbon linked group that does not hinder the enzyme,
 Z is any compatible nitrogen linked group that does not hinder the enzyme selected from the group consisting of NH; N-alkyl; N-aryl; N—C$_6$H$_4$SO$_3$H, and salts; N—(CH$_2$)$_x$CO$_2$H, salts, esters and amides; and N—(CH$_2$)$_x$SO$_3$H, and salts; wherein x is from 1 to 10, and R$^7$ is H, alkyl, aryl or any compatible group that does not hinder the enzyme.

5. A reagent as claimed in claim 1, wherein said heterocyclic group (Het) is of the formula:

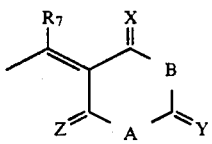

wherein
each of A and B independently is any compatible nitrogen linked group selected from the group consisting of: NH; N-alkyl; N-aryl; N—$C_6H_4SO_3H$, and salts; N—$(CH_2)_xCO_2H$, salts, esters and amides; and N—$(CH_2)_xSO_3H$ and salts; wherein x is from 1 to 10

X, Y and Z are selectable independently from the groups O, S and NR, where R is H, alkyl or any other compatible group that does not hinder the enzyme and $R^7$ is H, alkyl, aryl or any compatible group that does not hinder the enzyme.

6. A reagent as claimed in claim 1, wherein said n is in the range of 1 to 3 and the heterocyclic group (Het) is of the formula:

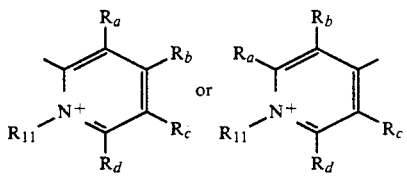

wherein:
$R^{11}$ is alkyl, aryl or any other compatible group that does not hinder the enzyme and $R^a$, $R^b$, $R^c$ and $R^d$ are independently selectable among the groups H, alkyl, aryl or any other compatible groups that do not hinder the enzyme and may be independent or linked to form saturated or unsaturated ring structures.

7. A reagent as claimed in claim 1, wherein said n is in the range 1 to 3 and the heterocyclic group (Het) is of the formula:

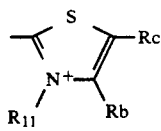

wherein:
$R^{11}$ is alkyl, aryl or any other compatible group that does not hinder the enzymes and $R^a$ and $R^b$, are independently selectable among the groups H, alkyl, aryl or any other compatible groups that do not hinder the enzyme and may be independent or linked to form saturated or unsaturated ring structures.

8. A reagent as claimed in claim 6, wherein said chromogenic group is capable of selective absorption onto cellulose and related polymers under mildly basic conditions.

9. A kit for the assay of an enzyme comprising:
a reagent comprising a substrate consonant with a given enzyme to be assayed, labelled with a chromogenic group which, on action of the given enzyme, is liberated to give a colored product, characterized in that the reagent is of the formula:

S—Z where S is a structural element recognized by the enzyme, and Z is a chromogenic group released by enzymatic cleavage of the S—Z bond, and further characterized in that the released chromogenic group is of the formula:

—X—Aryl—(CH=CR')$_n$—Het where Aryl is any aryl group, n is 0-3, R and R' are any compatible group that does not hinder the enzyme, Het is any heterocyclic group capable of extending the delocalization of electrons from the aryl group, and X is selected from the group —O— or —NR— where R is any compatible group that does not hinder the enzyme, said reagent being appropriate for assay of said enzyme and being packaged in a first container;
a stopping buffer packaged in a second container; and
a buffer suitable for incubation of said enzyme, said buffer being present with the reagent in said first container or being packaged in a third container.

10. A kit according to claim 9, wherein said reagent is in aqueous solution in said first container.

11. A kit according to claim 10, wherein said buffer is present in said first container.

12. A kit according to claim 9, wherein said stopping buffer comprises DABCO.

13. A kit according to claim 9, wherein the aryl group of said reagent is a phenol group incorporating solubilizing (hydrophilic) groups.

14. A kit according to claim 9, wherein the heterocyclic group (Het) of said reagent is of the formula:

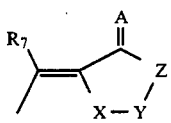

wherein
A is selected from the group O, S, or NR where R is H, alkyl or any other compatible group that does not hinder the enzyme,
X is selected from the group O, S, or NR where R is H, alkyl or any other compatible group that does not hinder the enzyme,
Y is selected from the group C=O, C=S, or C=NR where R is H, alkyl or any other compatible group that does not hinder the enzyme.
Z is any compatible nitrogen linked group that does not hinder the enzyme selected from the group consisting of NH; N-alkyl; N-aryl, N—$(CH_2)_x$-$CO_2H$, salts and esters; N—$(CH_2)_xNR_2$, and salts; N—$(CH_2)_xSO_3H$, and salts; and N—$(CH_2)_xNR_3X$, where R is alkyl, x is 1-6, and X is O, S, or NH,
and $R^7$ is H, alkyl, aryl or any compatible group that does not hinder the enzyme.

15. A kit according to claim 9, wherein the heterocyclic group (Het) of said reagent is of the formula:

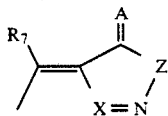

wherein:
- A is selected from the group O, S, or NR where R is H, alkyl or any other compatible group that does not hinder the enzyme,
- X is selected from the group C-alkyl, C-aryl, or any other compatible carbon linked group that does not hinder the enzyme,
- Z is any compatible nitrogen linked group that does not hinder the enzyme selected from the group consisting of NH; N-alkyl; N-aryl; N—$C_6H_4SO_3H$, and salts; N—$(CH_2)_xCO_2H$, salts, esters and amides; and N—$(CH_2)_xSO_3H$, and salts; wherein x is from 1 to 10,
- and $R^7$ is H, alkyl, aryl or any compatible group that does not hinder the enzyme.

16. A kit according to claim 9, wherein the heterocyclic group (Het) of said reagent is of the formula:

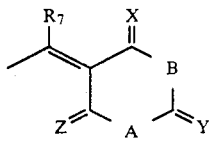

wherein
- A is any compatible nitrogen linked group selected from the group consisting of: NH; N-alkyl; N-aryl; N—$C_6H_4SO_3H$, and salts; N—$(CH_2)_xCO_2H$, salts, esters and amides; and N—$(CH_2)_xSO_3H$ and salts; wherein x is from 1 to 10
- X, Y and Z are selectable independently from the groups O, S and NR, where R is H, alkyl or any other compatible group that does not hinder the enzyme
- and $R^7$ is H, alkyl, aryl or any compatible group that does not hinder the enzyme.

17. A kit according to claim 9, wherein n in the formula for the reagent is in the range of 1 to 3 and wherein the heterocyclic group (Het) of said reagent is of the formula:

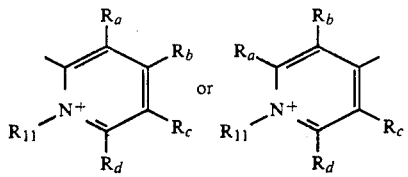

wherein
- $R^{11}$ is alkyl, aryl or any other compatible group that does not hinder the enzyme and $R^a$, $R^b$, $R^c$ and $R^d$ are independently selectable among the groups H, alkyl, aryl or any other compatible groups that do not hinder the enzyme and may be independent or linked to form saturated or unsaturated ring structures.

18. A kit according to claim 9, wherein n in the formula for the reagent is in the range of 1 to 3 and wherein the heterocyclic group (Het) of said reagent is of the formula:

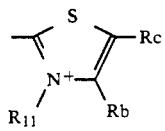

wherein
- $R^{11}$ is alkyl, aryl or any other compatible group that does not hinder the enzyme and $R^a$ and $R^b$, are independently selectable among the groups H, alkyl, aryl or any other compatible groups that do not hinder the enzyme and may be independent or linked to form saturated or unsaturated ring structures.

19. A kit according to claim 9, wherein X in the formula for the reagent is O and wherein the chromogenic group has a high affinity for cellulose or cellulose derivatives.

* * * * *